(12) United States Patent
Myers et al.

(10) Patent No.: US 6,714,874 B1
(45) Date of Patent: Mar. 30, 2004

(54) METHOD AND SYSTEM FOR THE ASSEMBLY OF A WHOLE GENOME USING A SHOT-GUN DATA SET

(75) Inventors: Gene W. Myers, Gaithersburg, MD (US); Arthur L. Delcher, Towson, MD (US); Ian M. Dew, McLean, VA (US); Michael J. Flanigan, Reston, VA (US); Saul A. Kravitz, Rockville, MD (US); Clark M. Mobarry, Silver Spring, MD (US); Knut Reinert, Washington, DC (US); Karin A. Remington, Gaithersburg, MD (US); Granger G. Sutton, Columbia, MD (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 09/526,131

(22) Filed: Mar. 15, 2000

(51) Int. Cl.$^7$ .............................. G06N 3/12; G06F 7/00; G06F 7/16
(52) U.S. Cl. ........................... 702/20; 707/102; 706/13
(58) Field of Search .................... 702/20, 195, 196, 702/150; 707/4, 6, 7, 102, 103 R; 712/10, 21, 26, 202; 435/6; 706/13

(56) References Cited

U.S. PATENT DOCUMENTS 5,966,712 A * 10/1999 Sabatini et al.

OTHER PUBLICATIONS

Anson and Myers, proceedings of the Third Annual International Conference on Computational Molecular Biology, Apr. 11–14, 1999, pp. 1–9.
Burkhardt et al., RECOMB 99: proceedings of the Third Annual International Conference on Computational Molecular Biology, Apr. 11–14, 1999, pp. 77–83.
Myers, Toward Simplifying and Accurately Formulating Fragment Assembly, Tech. Rep., Dept. of Computer Science, University of Arizona; also in: Comput. Biol. (1995) 2(2):275–290.
Bonfield et al., Nucleic Acids Research (1995) 23(24):4992–4999.
Burkhardt et al., q–gram Based Database Searching Using a Suffix Array (QUASAR) Recomb. (1999) pp. 77–83.
Chen et al., The Eighth Symposium on Combinatorial Pattern Matching (1997) pp. 206–223.
Gusfield, "Algorithms on Strings, Trees, and Sequences" Cambridge University Press, NY, USA (1997) pp. 263–278 and pp. 420–425.
Istvanick et al., System Sciences, Proceeding of the Twenty–Sixth Hawaii International Conference on Wailea, HI, USA Jan. 5–8, 1993, pp. 534–543.
Kececioglu et al., Algorithmica (1995) 13(1/2):7–51.
Manber et al., Siam Journal on Computing, Society for Industrial and Applied Mathematics (1993) 22(5):935–948.
Marth et al., Nature Genetics (1999) 23(4):452–456.
Myers, Computing in Science & Engineering (1995) 1(3):33–43.
Wu et al., "A Subquadratic Algorithm for Approximate Limited Expression Matching" Algorithmica, Springer Verlag, New York, NY, US (1996) 15(1):50–67.

* cited by examiner

*Primary Examiner*—Marjorie Moran
(74) *Attorney, Agent, or Firm*—Morrison & Foerster LLP

(57) ABSTRACT

The present invention provides methods and systems for assembling a genome from a shot-gun set of end sequenced DNA fragments. Specifically, the present invention provides a method of determining the genomic sequence (base sequence and orientation) of a complex genome using DNA sequence information generated from a collection of DNA fragments obtained from the genome. The present method is particularly useful in assembling genomes of at least 10 MB (up to 5 GB) and which are made up of at least 5% repetitive DNA sequences (up to 25% repetitive), but can be used also for smaller genomes with a lower percentage of repetitive DNA.

16 Claims, 6 Drawing Sheets

FIG. 4A

```
  ATACAT-C-AG-T--CGCAAAGA-CTTGT-CCG
1 T-.......T......C................
2 T..............-.................
3 T..............T.....A....G......
4 T..............T.....A....G......
5 .....G...C......G.........C...-.
6 ................G........A....-.
7 .........T....................T...
8 ..........T....A..................
```

FIG. 4B

```
11111111111111111N1111111111bkkkdgTkkKKKNAKKKKKKKK
TGATCTATACACTCGTC-TGGGGCTACGACTTACGAGGCATGATCCTGCAC TGAT-TATACACTCGTCGTGGGGCTACGACTTACGAGGCATGATCCTGCAC
KKKECMKKNKEKK:KKKKKKKIEKKKKKOKMKKKKKKLKKPKK5KAKKKKKK
```

METHOD AND SYSTEM FOR THE ASSEMBLY OF A WHOLE GENOME USING A SHOT-GUN DATA SET

RELATED PATENT APPLICATIONS

This application claims the benefit of Patent Application No. 60/154,593 filed Sep. 17, 1999 and Patent Application No. 60/183,758 filed Feb. 22, 2000.

FIELD OF THE INVENTION

The present invention relates to the field of genomic sequencing and assembly, providing methods for assembling a genome using a shot-gun data set of DNA sequences.

BACKGROUND OF THE INVENTION

The advent of automated DNA sequencing (Smith, L. M. et al., 1986, Nature 321, 674–679) and recent advances in scaling up of this technology (Adams et al., 1994, Nature 368, 474–475) have led to new approaches to determine the genome sequences of humans and other organisms. Classic approaches have included shot-gun sequencing of lambda inserts (~10–20 kbp) or cosmids (~40 kbp), and this approach has been successfully applied to certain large-scale projects, such as the genomes of *Escherichia coli* (Sofia et al., 1994, Nucleic Acids Res 22, 2576–2586), *Saccharomyces cerevisiae* (Levy, 1994, Yeast, 10, 1689–1706), *Caenorhabditis elegans* (Sulston et al., 1992, Nature 356, 37–41), and humans (Martin-Gallardo et al., 1992, Nature Genet 1, 34–39; McCombie et al., 1992, Nature Genet 1, 348–353). The shot-gun strategy is based on sequencing many small (on the order of 1–2 kbp), randomly chosen subclones of the lambda or cosmid clones. Typically, 300–500 bp of sequence is determined from one or both ends of the subclones. Enough sequence fragments must be obtained, however, and their positions distributed evenly enough so that all or most of the target DNA are covered by at least one fragment. Ideally, the coverage should be by as many fragments as are required to resolve ambiguities and provide confidence in the accuracy of the final consensus sequence.

Sequence assembly algorithms have been developed to reconstruct the original sequence from these fragments. The reconstruction process involves finding pairs of fragments that overlap, merging as many fragments together as possible, and creating a consensus sequence from the merged fragments. Sequence fragment assembly is a relatively straightforward programming problem, in the absence of complicating factors. There are assembly algorithms available, including XBAP (Gleeson and Staden, 1991, Comput Appl Biosci 7, 398), AutoAssembler (Applied Biosystems, Foster City, Calif.), GCG (Dolz, 1994, Methods Mol Biol 24, 9–23), the TIGR Assembler, and several others (reviewed in Miller and Powell, 1994, J Comp Bio 1, 257–269). Each of these algorithms has certain advantages and disadvantages and works reasonably well on lambda- or cosmid-sized assemblies. However, these algorithms typically do not perform well on reconstruction of an order or more of magnitude larger scale. A more recent assembly program, FALCON (Gryan, 1994, Genome Sequencing and Analysis Conference VI, abstract E/B-3 (Mary Ann Liebert, Inc., Larchmont, N.Y.)), uses a fast pairwise comparison method similar to that of the TIGR Assembler and can handle larger assembly projects, but still has a practical useful upper limit of about 10 MB. While certain other assembly programs could possibly be scaled up with some redesign effort, the functionality that many of these programs lack is a strategy to detect and handle repeat regions.

The lack of an adequate assembly engine has been one of the driving forces to maintain a cosmid-based genome sequencing strategy, even for megabase-scale projects. The major problems to be solved in reconstructing much larger assemblies include (1) a dramatic increase in the number of pairwise comparisons required, (2) the increased likelihood of encountering repetitive DNA that confounds true fragment overlaps with false overlaps, and (3) the increased probability of encountering chimeric clones that can cause false overlaps or mask true overlaps. In addition, many commentators have stated the whole genome shot-gun sequencing and assembly cannot be done with large genomes that contain repetitive elements (for example, see Green, 1997, Genome Research 7:410–417).

SUMMARY OF THE INVENTION

The present invention is based on the sequencing and assembly of the *Drosophila melanogaster* genome. During the sequencing of the genome, it became clear that existing methods used for assembling a genome using sequence information obtained from fragments of the genome would not work with large genomes and/or genomes with any significant degree of repeat sequence structure. The present invention provides a method and system that can be used to assemble the genome of any organism using a shot-gun data set of sequenced fragments.

The assembler of the present invention allows for the assembly of large and complex genomes (of greater than 10 Mbp and up to 5 Gbp) using a total shot-gun approach, even when there is significant amounts of repetitive DNA in the genome being assembled. Herein, we explain how the present assembler handles these complicating factors.

The present invention provides a new approach to assembling large genomes using a shot-gun data set of fragments. The basic design methodology of one embodiment of the assembler of the present invention is to:

1) Identify the repeats and leave them for last;
2) Assemble the unambiguously assemblable fragments first; and
3) Use all data available, including mate pair data, to resolve the repeat regions.

In one embodiment, the assembler of the present invention includes the following modules performing specific stages in the assembly of large genomes:

1) Screener: The Screener module identifies all sequences in the raw data which contain heterochromatic DNA or a known repetitive element. Examples of repetitive elements include rDNA and known interspersed repeats such as transposons.
2) Overlapper: The Overlapper module performs an "all against all" comparison of all fragments and their complementary sequences output by the Screener module. The Overlapper module identifies all overlapping fragments that meet a minimal overlap value within a maximum percentage of mismatch. For example, the Overlapper module can be set to identify all fragments that have overlapping sequences of at least about 40 bases and allowing no more than about 6% mismatching.
3) Unitigger: Using the fragment overlap data produced by the Overlapper module, the Unitigger module identifies all consistent sub-assemblies of fragments ("unitigs") and further identifies all sub-assemblies that cover unique DNA ("U-unitigs").
4) Scaffolder: The Scaffolder module uses the U-unitig data in conjunction with mate pair data to generate an ordered framework ("scaffold") of the genome of U-unitigs. Input to the Scaffolder module includes mate pair data from different size fragment pairs. For example, fragment pairs can be generated from 2 kbp, 10 kbp, and 150 kbp clone inserts. The Scaffolder module confirms the ordering of U-unitigs through the use of two or more confirming mate pairs. In a scaffold, any set of U-unitigs that are overlapping are merged to form a single contig.

5) Repeat Resolution: The Repeat Resolution module fills gaps between the contigs produced by the Scaffolder module. The Repeat Resolution module employs an iterative process that first uses the highest quality data, such as doubly anchored mate pairs, and then proceeds to use data with more uncertainty, such as overlap-path, confirmed singled anchored mate pairs. Finally, the Repeat Resolution module employs a "greedy path" completion strategy that uses quality values to fill the repeat-induced gaps.

6) Consensus: The Consensus module generates a consensus sequence of the genome based on the information generated by the Scaffolder and Repeat Resolution modules. The Consensus module builds a Bayesian single nucleotide polymorphism ("SNP") consensus sequence using quality values obtained through the assembly process.

A detailed description of each of these elements and the operation of the algorithm is provided below. All references cited herein are incorporated by reference in their entirety.

BRIEF DESCRIPTION OF THE DRAWINGS

FIG. 4A provides a multiple sequence alignment.

FIG. 4B provides a pairwise sequence alignment combined with quality scores.

DETAILED DESCRIPTION OF INVENTION

Definitions

Figure 1:
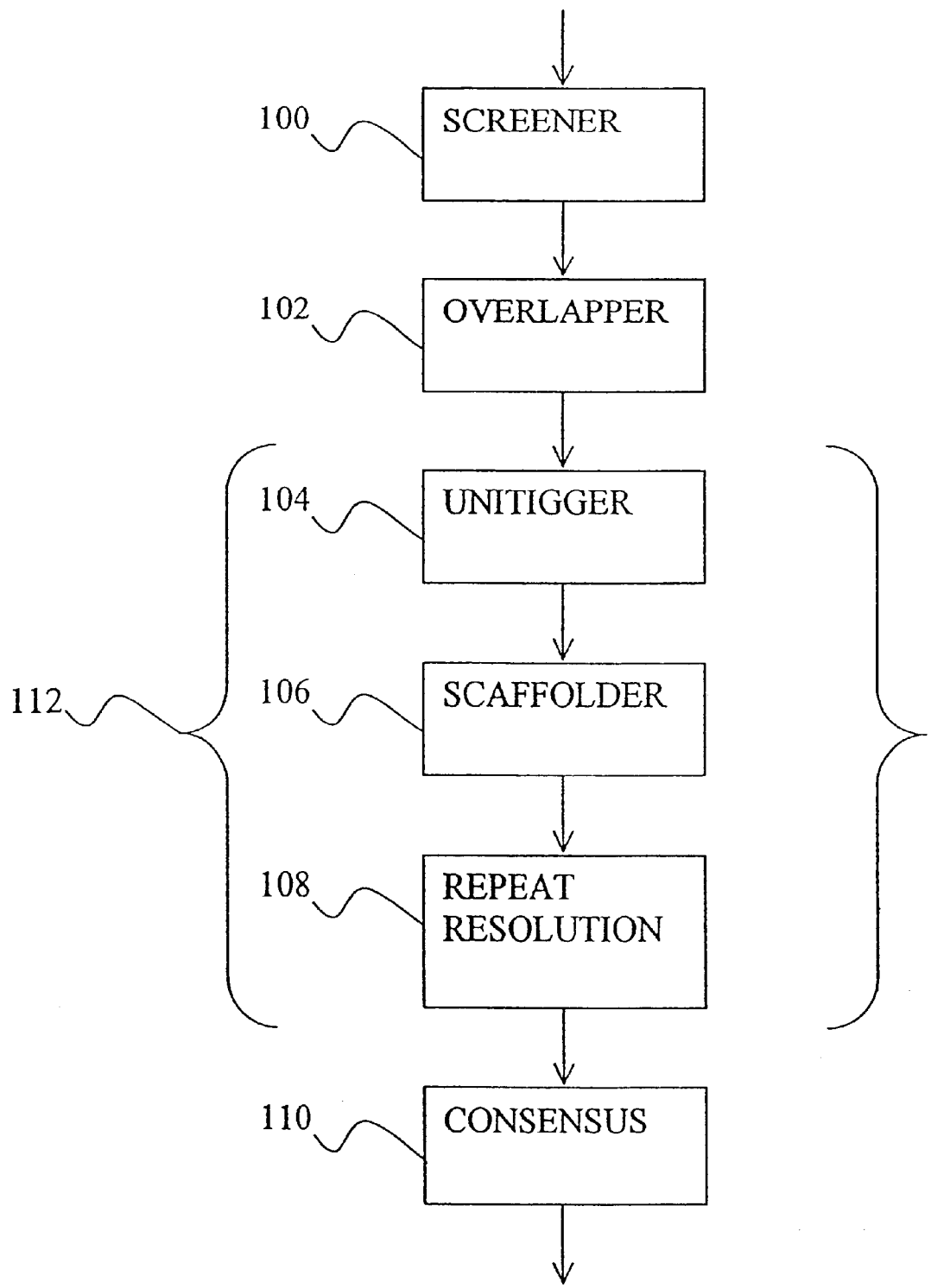
FIG. 1 provides a flow diagram of the assembly process flow according to one embodiment of the invention.

As used herein, the term "fragment" refers to a short stretch of DNA sequence information randomly selected from a genome. It is a purpose of this invention to determine the nucleic acid sequence of an organism's genome by assembling the data derived from a plurality of fragments.

The term "fragment-end" refers to either the prefix (5' end) or suffix (3' end) of a fragment.

The term "fragment overlap" (or "overlap") refers to a relationship between two fragments where there is a matching sequence region (either the original DNA sequence or its Watson-Crick complement) in the fragments that is terminated in each direction by the end of a fragment. The matching sequence region may contain some number of differences over its length, generally expressed in terms of the percent of base substitutions, insertions, and deletions.

The term "dovetail overlap" refers to an overlap relationship between two fragments where only one fragment-end from each fragment is involved in the overlap. A "dovetail run" of fragments and dovetail overlaps is a simple path, terminated by a fragment on either end, where each fragment-end in the run is adjacent (via a dovetail overlap) to zero or one other fragment-ends. A "dovetail path framework" is a non-cyclic sub-graph of a fragment overlap graph that satisfies properties described in E. Myers, "Toward Simplifying and Accurately Formulating Fragment Assembly," J. Computational Biology, Vol. 2, No. 2, 1995.

The term "containment overlap" refers to an overlap relationship between two fragments where the sequence of one fragment is wholly contained in that of the other fragment. A "containment run" of fragments and containment overlaps is a simple path, terminated by a fragment on either end, where each fragment has a containment relationship to and from at most one other fragment. The term "contained fragment" refers to a fragment that whose sequence is wholly contained in that of another fragment by a containment overlap. A locally contained fragment is a fragment that is contained by at least one other fragment in a given subset of the shot-gun data set. A globally contained fragment is a fragment that is contained by at least one other fragment in the entire shot-gun data set.

The term "fragment overlap graph" refers to a graph where vertices represent fragments or fragment-ends and edges represent overlaps. A "reduced fragment overlap graph" is a sub-graph of the all-against-all fragment overlap graph produced by the Overlapper module in which redundant, repetitive, non-useful, and spurious overlap edges have been removed. A correctly reduced fragment overlap graph contains all possible correct fragment assemblies.

The term "chunk" refers to a maximal sub-graph of the reduced fragment overlap graph that consists of only non-contained fragments and dovetail overlap edges, where each overlap edge is the only dovetail overlap edge in the reduced fragment overlap graph adjacent to each fragment-end in the overlap.

The term "unitig" refers generally to a unique sub-assembly of fragments, and specifically to a particular dovetail path framework of the reduced fragment overlap graph where the dovetail path is a chunk of the reduced fragment overlap graph. A unitig differs from a chunk by including contained fragments and dovetail edges to them. The term "U-unitig" refers to a unitig belonging to a unique region on a genome. The term "R-unitig" is used to refer to a unitig that cannot be determined to belong to a unique region on the genome.

The term "insert" refers to a short piece of DNA randomly selected from a genome and replicated in a cloning vector. In one embodiment, the size of an insert is known to at least a first approximation and fragment information is collected from both ends of the insert.

A "mate pair" includes fragment information from both ends of an insert in combination with the insert's size, such that the separation between the two sequenced fragments is known to at least a first approximation. The term "mate pair bundle" refers to a set of consistent pairwise mate relationships that are confirmed between a pair of unitigs.

The term "microsatellite DNA" refers to a DNA sequence comprising an approximately-repeating motif of short length.

The term "sequencing quality value" refers to a value assigned to a sequenced base representing the confidence that the base was sequenced correctly. The term "overlap quality value" refers to a calculated value reflecting the probability that two overlapping sequences come the same or different genomic regions. Except where defined otherwise, the term "quality value" refers to sequencing quality value.

The term "shot-gun data set" refers to a data set including a plurality of fragments and associated mate pair information.

Lastly, as used herein, the term "scaffold" refers to an ordering of unitigs, indicating their relative order, position, and orientation.

Shot-Gun Data Set

In one embodiment, the raw data input into the assembler of this invention is a shot-gun data set, which includes nucleic acid sequence information obtained from a plurality of relatively short pieces of DNA, called "inserts." A shot-gun data set can be generated from the genomic DNA of any organism by first generating a plurality of inserts, and then obtaining nucleic acid sequence information for each insert. One method of generating the plurality of inserts is to randomly shear the genomic DNA, resulting in a random breaking of the genomic DNA into random pieces. Methods of random shearing are well known to these skilled in the art. Examples include sonication and passage through a syringe needle.

Once the inserts are generated, the nucleic acid sequence of each insert is then determined. Current sequencing technology, such as that employed by the ABI PRISM® 3700 DNA Analyzer (PE Biosystems, Foster City, Calif.), allows for about 500 bp of sequence data to be reliably determined from each end of a given insert. For example, a 2 kbp insert can reliably yield 500 bp of sequence data from each end, leaving a 1 kbp gap of unsequenced DNA between each sequenced fragment. As discussed above a "mate pair" includes fragment sequence information from both ends of an insert in combination with the insert's size, such that the separation between the two sequenced fragments is known to at least a first approximation. The input to the assembler of this invention generally includes the entire set of mate pairs generated in the shot-gun data set.

In one embodiment, the assembly method of the present invention relies on the use of a shot-gun data set generated from at least two, and preferably three, different sizes of DNA inserts. The sheared DNA can readily be separated into discrete sized pieces using methods known in the art, such as by gel electrophoresis. The choice of the sizes can vary, as long as one size is suitably large relative to at least one of the other sizes. In one embodiment, three sizes of inserts are employed: 2 kbp ("short" inserts, suitable for growth in a plasmid vector), 10 kbp ("long" inserts, suitable for growth in a lambda vector) and 150 kbp ("BAC" inserts, suitable for growth in a bacterial artificial chromosome).

In one embodiment, a larger number of shorter-sized than larger-sized inserts may be used to generate the shot-gun data set. The ratio of the number of shorter-sized to longer-sized inserts can vary based on the size of the genome being sequenced, the amount of repetitive elements present in the genome and the average, minimum, and maximum length of the repeat elements. In one embodiment, two sizes are employed and a ratio of 2:1 (short to long) is used, although other numbers of sizes and ratios are contemplated.

It is important to assure complete coverage of the genome by the fragments that are sequenced. Accordingly, the shot-gun data set can provide about 10-fold coverage of the genome of the organism being sequenced.

The shot-gun data set may include a quality value associated with the sequence data generated for each fragment. Additionally, the shot-gun data set may include a quality value associated with each base pair sequenced. In various embodiments, the shot-gun data set includes sequence information with an associated quality value of 90% or greater, preferably 95% or greater, and more preferably 98% or greater accuracy. Alternatively or additionally, the shot-gun data set includes sequence information with an average read length of about 400 bp or greater, preferably 450 bp or greater, and more preferably 500 bp or greater.

In one embodiment, the input to the first module of an assembler of this invention, the Screener module, is the shot-gun data set.

Screener Module

Referring to FIG. 1, the Screener module 100 is the first step of this embodiment of the assembler of this invention. The input to the Screener module 100 includes the sequence information from the shot-gun data set and a screen item library having a set of screen items. The Screener module 100 identifies the presence of screen items in the shot-gun data set so that they do not interfere with the functioning of other modules.

A screen item is a data structure used to represent a known element, such as a contaminant or a repeated sequence, such as rDNA or a transposon, the sequence of which could corrupt intermediate and final assembly results. A screen item typically includes the element's sequence and associated parameters for matching the sequence to fragment sequences, such as minimum interval length, maximum percentage difference, and how to handle a match. For each screen item, the Screener module 100 identifies intervals of fragment nucleotide sequences which match intervals of the screen item's nucleotide sequence at or above the minimal interval length and at or below the maximum percentage difference. The output of the Screener module 100 includes a set of annotations to the sequence information of the shot-gun data set, each annotation indicating the presence, location, and direction of a screen item matching a fragment sequence, as well as an indication of how the match should be handled by subsequent modules, such as whether or not the match should be "masked." In one embodiment, an annotation may further include the actual percentage difference of the match.

In one embodiment, the Screener module 100 detects all matching intervals when screen item parameters specify minimum interval lengths greater than or equal to about 40 bases and maximum percent differences less than or equal to about 15%, although other values may be used.

In one embodiment, the Screener module 100 first prepares a set of fragment nucleotide sequences to be searched by populating a search table with sequence data from the set. The set may include all of the sequence data in the shot-gun data set. In an alternative embodiment, the set includes only a subset of the sequence data in the shot-gun data set. In a further embodiment, the shot-gun data set is divided into subsets. In yet a further embodiment, the subsets are processed in parallel.

In a further embodiment, the search table includes an indexed set of linked lists of all overlapping k-mers (k contiguous bases) of a set of fragment nucleotide sequences, where each element (k-mer) in the set of linked lists references the fragment and position in the fragment sequence where it occurs. In one embodiment, k=12.

After this data structure is populated, the Screener module 100 compares each screen item against the search table. A parameter q is calculated for each screen item based on the screen item's parameters. In a typical embodiment, $q \leq k$. In one embodiment, q is calculated to be the largest possible value such that all bases that match in a minimum length interval will occur in at least one matching q-mer (q contiguous bases) when a maximum allowed number of errors are distributed evenly over the interval. The Screener module 100 then traverses the sequence of the screen item from the first base to the last and looks up each q-mer of the sequence in the search table. The Screener module 100 may simultaneously look up the reverse complement of each q-mer.

In a further embodiment, the Screener module 100 looks up not only the q-mer itself, but also inexact matches of the q-mer. For example, the Screener module 100 can generate and look up the set of all oligomers that differ from the q-mer by exactly one substitution, insertion, or deletion. This set is defined as the "1 neighborhood" of the q-mer. The Screener module 100 can also look up inexact matches of the reverse complement of the q-mer.

When a k-mer is found which sufficiently matches the q-mer, the "diagonal" of the hit is calculated. For the purposes of this invention, the diagonal is equal to the position of the q-mer in the screen item sequence minus the position of the k-mer in the fragment to which the k-mer belongs. Also, a data structure known as a hit object is generated. In one embodiment, the hit object includes the identity of the fragment to which the k-mer belongs and the position within the fragment where the match occurred. The newly-generated hit object is then stored in another data structure called the hit collector.

The hit collector may be an indexed set of stacks. In a further embodiment, the hit collector is indexed by diagonal, with one stack corresponding to each possible diagonal. In this embodiment, the number of stacks is equal to the length of the longest fragment in the set of fragment nucleotide sequences, which is the number of possible diagonals. In this embodiment, the newly-generated hit object is pushed on the stack corresponding to that hit's diagonal. In this manner, the hits on any given stack in the hit collector will be randomly interleaved with respect to the set of fragments, but the hits for each fragment will be in reverse order with respect to position in the fragment sequence.

As used herein, the "current diagonal" is defined as the stack in the hit collector corresponding to the diagonal of the q-mer's first base position in the screen item sequence. After a q-mer is looked up and its hits pushed onto the appropriate stacks, the current diagonal cannot receive additional hits. The data in this stack are therefore ready to be processed further.

In one embodiment, the data in the current diagonal are transferred to a data structure known as a hit analyzer. The hit analyzer can include a ring of sparse arrays. In one embodiment, the number of sparse arrays is one or two plus the number of errors allowed when matching the screen item over a minimum length interval. In an alternate embodiment, the number of sparse arrays is set lower, increasing speed at the possible expense of missing acceptable matches. The data from the current diagonal are then used to populate a sparse array in the hit analyzer designated as the current sparse array.

Each sparse array of the hit analyzer may be indexed by fragment and subindexed by block within each fragment. In this embodiment, blocks are uniform length, overlapping intervals covering the length of the fragment sequence. Blocks overlap each other by half their length. In another embodiment, block length is equal to two times the largest minimum interval length in the screen item library. Transferring data from the hit collector to the sparse array effectively de-interleaves the data with respect to fragments. A description of block addressing can be found in Burkhardt, Stefan, et al. "q-gram Based Database Searching Using a Suffix Array (QUASAR)", RECOMB proceedings, pp. 77–83, 1999.

Once the current sparse array is populated with data from the current diagonal, the oldest sparse array is then analyzed. For each block in the oldest sparse array that contains hit objects, hit objects are aggregated over corresponding blocks in the other sparse arrays of the hit analyzer. Within each block, if the number of matching bases exceeds a computed threshold for the number of sparse arrays on which matched bases were found, the fragment-screen item interval within which the matched bases occurred is deemed a candidate match. A separate threshold may be computed for each number of sparse arrays in which corresponding blocks contain matching bases. In one embodiment, thresholds may be computed to guarantee that all acceptable matches are deemed candidate matches. In other embodiments, thresholds may be set higher to increase speed at the possible expense of missing acceptable matches.

Candidate matches that reference the same fragment, screen item, and direction may be combined if the proximity of the intervals is such that they are likely to be parts of the same, longer match. After a screen item is processed in this fashion, candidate matches are further processed to extend and confirm them. In one embodiment, a banded local alignment dynamic programming algorithm is applied to each candidate match to detect all local intervals that have sufficient length and a sufficient local alignment score. All sufficiently long and high-scoring local alignments are reported as matches, and the shot-gun data set is annotated with the proper information. Other modules can consult these annotations to determine whether or not to include the annotated sequences in their analyses.

In one embodiment, the Screener module 100 employs a method for determining if a fragment comprises an approximately-repeating motif of short length, known as microsatellite DNA. This method can detect the presence of microsatellite DNA even when the motif is not known beforehand.

In one embodiment, the method is performed as follows: Given threshold d and string s, find a short string x such that for some $k \geq 0$ and $1 \leq p \leq |x|$, $\text{diff}(x^k x_{1 \ldots p}, s) \leq d$ where diff(A,B) is the edit distance between A and B, and $x^k$ is k copies of x concatenated together, and $x_{1 \ldots p}$ is the substring of x consisting of its first p characters. If there are several choices of x satisfying the criterion, return those realizing the smallest edit distance.

The approach uses tuple-based filtration to determine quickly if such an x does not exist, so that little time is expended in the common case where the string does not have such property. The filtration also quickly eliminates many choices of x that do not give the property. Filtration methods have been used before in comparing strings to each other for the purposes of finding matches (e.g. Ukkonen 1985 and Manber and Wu 1986), but never before to this problem.

Other work on the problem includes the dynamic programming approach of Sagot (1995) and the heuristic work of Benson (1996). In one embodiment, the invention applies tuple-based filtration followed by dynamic programming verification of a microsatellite.

The first layer is to count all k-mers for some choice of k. If s is a microsatellite of x at the level of d or fewer differences, then the sum of the number of occurrences of the most frequent $|x|$ k-mers must not be less than lim=$|s|$+1−k (d+1). In one embodiment for detecting microsatellite motifs up to 6 bases in length, k=3.

If the first condition is satisfied, then the string may be a microsatellite and further probing is performed. Any possible x must contain a k-mer, such that the sum of the number of occurrences of it and the next $|x|$−1 next most frequent k-mers is not less than lim. We call such k-mers essential and we explore x involving such k-mers.

Consider an essential k-mer, p. If $|x| \leq k$ then the sum of the frequencies of the first k+1−$|x|$ cyclic shifts of p must not be less than lim. Otherwise, one explores all possible extensions of p to give a string of length $|x|$ being careful not consider periodic choices or those explored for previously explored essential k-mers. Any choices of an x that satisfy this last filtration step are then examined via wrap around dynamic programming (Myers & Miller 1989, Landau et al. 1991) to see if x is indeed a microsatellite and if so, how good a model it is for the one that constitutes the subject string s.

Overlapper Module

Referring again to FIG. 1, the Overlapper module 102 of this embodiment follows the Screener module 100. The Overlapper module 102 takes a screened set of fragment nucleotide sequence information and finds overlaps between pairs of fragments that satisfy certain criteria. Two fragments are said to overlap if there is a matching sequence region in the fragments that is terminated in each direction by the end of a fragment. Either fragment may be reverse complemented. Typical match criteria are a minimum length of matching region and quality of match region as measured by the number of errors in the match. The number of errors in the match can also be based on the quality values associated with the sequence.

For example, the Overlapper module 102 locates all overlaps of 40 bp and longer that contain a number of errors that is at most 6% of the length of the matching region. In one embodiment, an overlap between two sequences is determined by a two step process: initiation and extension. An overlap is initiated when the two sequences share an exact match of a certain threshold length S. In one embodiment, S=20 bp. An exact match is identified by storing all S-mers of a set A of fragments in a hash table. Then for another fragment, ƒ, all S-mers in ƒ can be looked up in that hash table. The matches are then grouped according to which fragment in A they matched, and overlapping S-mer matches are merged into maximal exact-match regions. In one embodiment, matches are stored in a small, separate hash table, with one entry for each fragment in set A, with each entry being a sorted linked list of exact-match regions. Maximal exact-match regions also can be identified using suffix trees. Matches for the reverse complement of ƒ are found in the same fashion.

Each exact-match region can initiate an overlap. Once initiated, the overlap is extended in both directions. In one embodiment, the overlap is extended using the greedy O(kn) algorithm of Ukkonen and Myers, in which k is the maximum number of errors that can be in the match and n is the sequence length from the exact-match region to the closest fragment end. The extension explores a range of diagonals from the end of the exact-match region, keeping track of the longest-possible extension on each diagonal for a given number of errors. If the number of errors is too high for the extension length, based on a probabilistic model of errors, that diagonal is abandoned. The entire extension fails when the range of viable diagonals becomes empty. For example, a probability model of independent errors can be assumed, yielding a binomial distribution on the probability of e errors in a sequence of length m. If that probability falls below a threshold, e.g., $10^{-6}$, the given diagonal is abandoned. Other probability models incorporating quality values also can be used.

The Overlapper module 102 uses the annotation data from the Screener module 100 to determine which intervals of the fragment data should be "masked" from the overlap process and should not be used to initiate an overlap. Specifically, if an S-mer extends sufficiently into a masked region, that S-mer is not used to initiate an overlap. In one embodiment, the masked intervals can be included in an overlap if other intervals of the fragment initiate the overlap, which then is extended into the masked region. In this embodiment, fragment intervals annotated but not masked by the Screener module 100 can initiate an overlap.

In another embodiment, the output of the Overlapper module 102 can include all valid overlaps within the specified mismatch limit. Alternatively, the Overlapper module 102 can exclude all overlaps that contained a sufficient portion of a screened region.

Unitigger Module

Still referring to FIG. 1, the Unitigger module 104 of this embodiment follows the Overlapper module. The Unitigger module 104 takes the all-against-all fragment overlap data produced by the Overlapper module 102 and uses this to produce all consistent sub-assemblies of fragments (unitigs) and further identify all sub-assemblies that correspond to unique regions of DNA (U-unitigs) in a genome. The all-against-all fragment overlap data is implicitly a graph, where, in one embodiment, an explicit representation treats the ends of each fragment as a vertex pair and each overlap as an edge.

In one embodiment, the unitigs and U-unitigs are produced by a four-step process performed on the fragment overlap graph: localization, reduction, chunking, and polishing, where the chunking and polishing steps may proceed iteratively. The localization step brings the fragments and their overlaps together into an adjacency list representation. The reduction step eliminates redundant, repetitive, and spurious overlap edges thus significantly reducing the set of overlap edges to a skeleton of essential edges that represent all possible correct assemblies of the fragments. The chunking step collapses the fragments as vertices into a smaller number of sub-graphs as vertices, by identifying unitigs in the fragment overlap graph, and distinguishes U-unitigs from non-U-unitigs. The resulting collapsed graph is called the unitig overlap graph. The polishing step reduces and annotates the unitig overlap graph. The polishing step classifies and operates on certain types of fragments and overlaps in the unitig overlap graph. These may be marked or removed. The polishing and chunking steps may proceed iteratively until the number of changes falls below a predetermined threshold.

The localization step produces an adjacency list representation of the fragments and overlaps and performs appropriate permutations of the vertices and edges of the graph in computer memory. This localizes in computational memory the fragments and overlaps that are near each other in the genome, thus rendering the graph suitable for rapid traversal and editing.

The reduction step removes certain overlaps that are not useful because of the small amount of information they contribute relative to the large amount of computational complexity they add. In one embodiment, the reduction step employs a "Double Adjacency Threshold" fragment overlap graph reduction method. The adjacency list of each fragment-end is sorted by expected importance to the assembly, for example from longest to shortest ("thickest" to "thinnest") in terms of the length of sequence in the overlap. Next, both fragment-ends of each overlap edge are inspected to see if their position in the adjacency list of each fragment-end is beyond a predetermined threshold. If both fragment-ends of the edge are beyond the threshold, then the edge is removed as not useful. In one embodiment, the Unitigger module 104 uses a double adjacency threshold that is the maximum value of 200, or twenty times the expected sampling coverage of the genome.

Figure 2A:
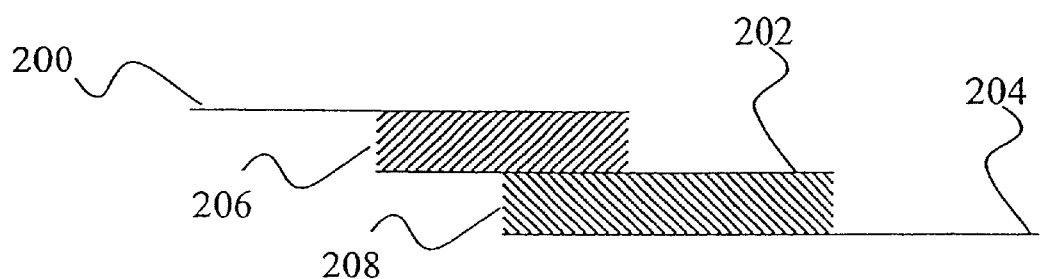
FIG. 2A provides a schematic representation of three overlapping fragments.

In one embodiment, the Unitigger module 104 reduces the all-against-all graph towards the minimal sub-graph by a method called chordal graph reduction. One method of chordal graph reduction is described in E. Myers, "Toward Simplifying and Accurately Formulating Fragment Assembly," J. Computational Biology, Vol. 2, No. 2, 1995. In chordal graph reduction, an edge representing an overlap is removed from the graph when that overlap can be transitively inferred from two other overlaps. FIG. 2A illustrates a transitively inferable overlap. In this figure, three fragments, fragment A 200, fragment B 202, and fragment C 204, overlap each other. The overlap between fragment A 200 and fragment B 202, as designated in this figure, is the A^B overlap. Other overlaps are similarly designated. For the purposes of this invention the A^B and B^C overlaps are considered thick relative to the thin A^C overlap.

Figure 2B:
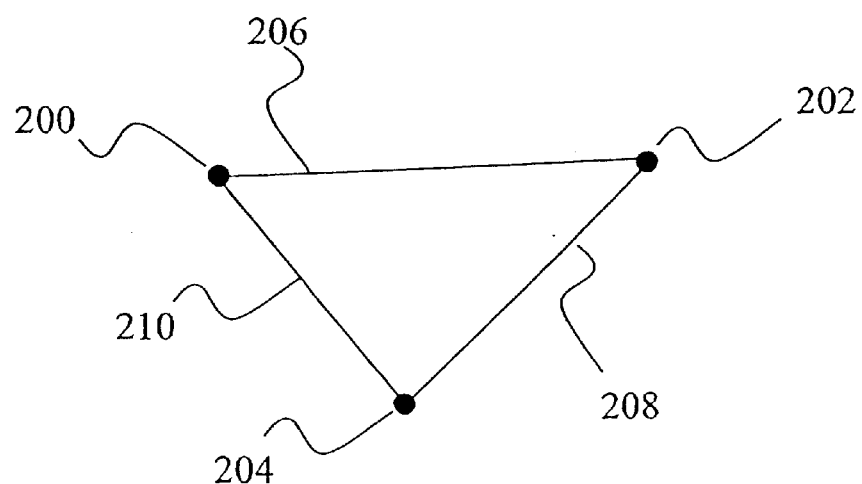
FIG. 2B provides a schematic representation of a graph representing three overlapping fragments.
Figure 2C:
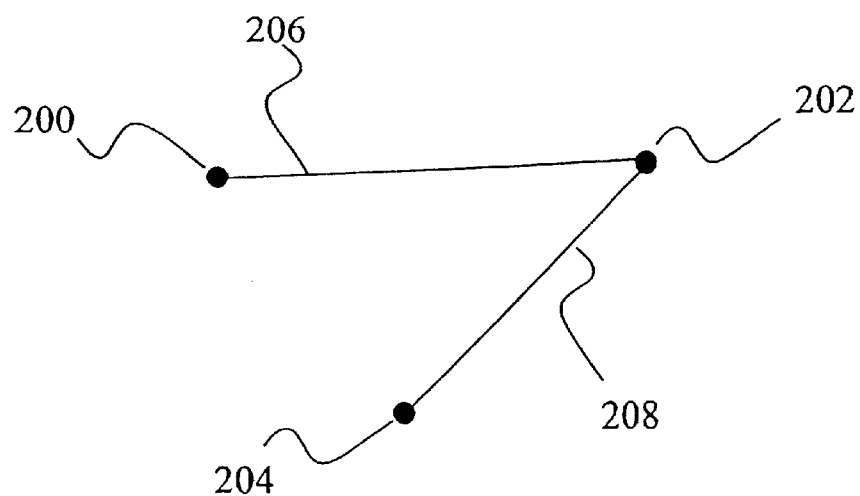
FIG. 2C provides a schematic representation of a reduced graph representing three overlapping fragments.

FIG. 2B is a representation of a graph illustrating the overlaps between the three fragments 200, 202, and 204. The edge 206 represents the A^B overlap, the edge 208 represents the B^C overlap, and the edge represents the A^C overlap. In this figure, the AAC overlap can be transitively inferred from the A^B overlap 206 and the B^C overlap 208. When performing transitive graph reduction, the Unitigger module 104 removes the edge from the graph, resulting in the graph illustrated in FIG. 2C. In this reduction, the thin A^C overlap is removed, leaving the thicker A^B and B^C overlaps. In practice, the existence of these overlaps may be evaluated to within a specified error tolerance consistent with the expected sequencing error.

Transitively inferable overlap edge reduction can be accomplished by any of several schemes, which vary in their aggressiveness. Each scheme involves choosing a consistent suite of fragment triplet topologies to transitively reduce the graph. Each fragment triplet topology for transitive overlap removal involves three fragments and three overlap edges. One of the edges represents a thin overlap that can be inferred from the other two thicker overlaps. A consistent suite is chosen so that: 1) the removal of an edge does not remove a possible correct assembly, and 2) the order of single edge removals is non-cyclic—that is, a transitive edge could not have caused the removal of an edge used for its removal if the order of single edge removals was changed.

The fragment triplet topologies for transitive overlap edge confirmation satisfy a general principle. In general, given three fragments, F1, F2, and F3, and overlaps F1^F2, F2^F3, and F1^F3, then the overlap F1^F3 is transitively confirmed if the sequence in the overlap F1^F3 is contained in the sequence in the overlaps F1^F2 and F1^F3. Note that that there are situations that transitive confirmation can be cyclic without further restrictions.

In the following examples, confirming fragment triplet topologies are classified with a three letter code of the form X-YZ where X encodes the type of a "candidate" overlap confirmed by path following an overlap of type Y, to the middle fragment, then following an overlap of type Z. The overlap types X, Y, and Z can take values: D for a dovetail overlap edge, T for a containment overlap edge to a contained fragment from a containing fragment, and F for a containment overlap edge from a contained fragment to a containing fragment.

A path following version of transitively inferable dovetail overlap edge removal for the D-DD topology is created by allowing the candidate dovetail overlap to be inferred from a dovetail run, which aligns the candidate overlap's fragments consistently with the candidate overlap. The inferred overlap edge can then be marked for removal or removed immediately from the graph.

A path following version of transitively inferable containment overlap removal for the T-TT topology is created by allowing the candidate containment overlap to be inferred from a containment run, which aligns the candidate overlap's fragments consistently with the candidate overlap. The inferred overlap edge can then be marked for removal or removed immediately from the graph. The F-FF topology is equivalent to the T-TT topology.

A path following version of transitively inferable dovetail overlap removal for the D-DT topology is created by allowing the candidate dovetail overlap to be inferred from a dovetail run whose last fragment starts a containment run, which together align the candidate overlap's fragments consistently with the candidate overlap. The inferred overlap edge can then be marked for removal from the graph. The D-FD topology is equivalent to the D-DT topology.

One embodiment of a consistent suite of fragment triplet topologies for transitively inferable overlap removal is called the "containment flattening suite". In general, given three fragments, F1, F2, and F3, and overlaps F1^F2, F2^F3, and F1^F3, then the suite of overlap topologies to transitively remove F1^F3 requires: 1) the overlap of F1 and F3 to be contained in the middle fragment F2; and 2) the middle fragment F2 not to be contained by F1 or F3. The suite of fragment triplet topologies used for transitive reduction are: D-DD, D-DT, D-FT, and T-FT. The suite is called the flattening suite because the surviving containment edges tend to be those that connect contained fragments to non-contained fragments.

Another embodiment of a consistent suite of fragment triplet topologies of transitively inferable overlap removal is called the "containment stacking suite". The suite of fragment triplet topologies used for transitive reduction are: D-DD, D-DT, and T-TT. The suite is called the stacking suite because the surviving containment edges tend to be those that connect contained fragments to the smallest containing fragment. An implementation of this suite does not need F-type containment edges.

One implementation of transitive graph reduction includes reduction using the D-DD and D-DT topologies. The D-DD topology reduction is critical to the identification of chunks. The D-DT topology reduction is critical to the identification of chunks in an incremental manner and placing the maximum number of contained fragments in unitigs. The remaining topology reductions are not necessary for chunking, but are useful for reducing the size of the graph.

In one embodiment, a global (i.e., performed on an entire shot-gun data set) method of performing transitive graph reduction is performed in three phases. First, the contained status of all fragments is determined. Second, transitive graph reduction is performed on the sub-graph of non-contained fragments and the dovetail edges connecting them. Third, transitive graph reduction is performed on the remaining graph using the chosen suite of reduction topologies, but with the restriction that dovetails between non-contained fragments are protected from further removal. Previously-known methods of graph reduction do not perform the third phase.

In another embodiment, the edges are not removed immediately but are marked as transitively removable. In this embodiment, the edges remain available to be used in fragment triplets to remove other edges. By contrast, if an edge is removed immediately, inferring its prior existence requires the traversal of paths of overlaps through fragments.

In another embodiment, incremental (i.e., performed on a complete collection of subsets of an entire shot-gun data set, presented in arbitrary order) transitive graph reduction is accomplished by successively merging pairs of overlap graphs and then transitively reducing the resulting graph. This technique relies on following paths of overlap edges through fragments to reconstruct previously removed overlap edges. The prior art does not support incremental transitive graph reduction.

The chunking step identifies the chunks of non-contained fragments and dovetail edges after the fragment overlap graph has been reduced. Edges internal to a chunk are labeled as "intra-chunk". Each candidate intra-chunk edge must be the only dovetail overlap edge in the reduced fragment graph adjacent to each fragment-end of the candidate edge. In addition, a reduced graph produced incrementally, in particular not using the global organization, defers an extra requirement to the identification of intra-chunk edges. In one embodiment, which uses incremental transitive graph reduction and reduces the D-DT topology, intra-chunk edges may not connect fragment-ends that are "dirty" by virtue of a conflict in contained fragment placement. A contained fragment-end is dirty when it is adjacent by a dovetail overlap with a non-contained fragment-end. A non-contained fragment-end is dirty when it is either adjacent by a dovetail overlap to a contained fragment, or adjacent, by a containment path, to a dirty contained fragment-end. A containment relationship between fragment-ends is a further refinement of a containment relationship between fragments. When a containment overlap involves the reverse complement of exactly one of the fragment sequences, the containment relationship is between the prefix (suffix) of the container and the prefix (suffix) of the contained fragment. When a containment overlap does not involve the reverse complement of either fragment sequence (or involves the reverse complement of both fragment sequences), the containment relationship is between the prefix (suffix) of the container and the suffix (prefix) of the contained fragment.

After the chunks are identified, "containment path selection" is performed. This is a temporary graph reduction to help identify dovetail path frameworks. When the chunks of the reduced fragment overlap graph are identified, every contained fragment is inspected to determine if all overlap paths connecting the contained fragment, possibly through other contained fragments, that terminate at the first non-contained fragment, are to the same chunk. If so, then only one overlap path connecting the contained fragment to the chunk is retained to facilitate the construction of dovetail path frameworks. Contained fragments that do not qualify for this reduction, that is, they have paths to disparate chunks, are used as the seed fragments to build their own dovetail path frameworks from the remaining contained fragments.

In one embodiment, overlap edges that are removed in containment path selection are not permanently removed, but remain available for use by any of the previously described graph reductions, if they are performed again.

After containment path selection, each maximal dovetail path framework sub-graph becomes a vertex of a unitig graph (i.e, a unitig). The unitig overlap graph inherits the overlap edges connecting unitigs to represent possible assemblies of unitigs.

After unitig generation, the Unitigger module 104 then classifies whether each unitig comes from a region on the genome having a unique or repetitive sequence. The Unitigger module 104 distinguishes unique from repetitive unitigs using a statistic related to the fragment arrival rate. Given a unique region of the genome and a set of fragments randomly sampled from that region, the expected distance in base pairs between fragments is the total number of fragments in the set divided by the length of the region. When the region is the entire genome, this expected average separation between fragments is called the global fragment arrival rate. A unitig covering a repetitive region will have a higher arrival rate than a unitig covering a unique region. For each unitig having a sufficient number of fragments, the Unitigger module 104 estimates its arrival rate and compares this to the global fragment arrival rate. If the estimated arrival rate is consistent with the global fragment arrival rate, then the Unitigger module 104 designates the unitig as a unique unitig, also known as a U-unitig. In one embodiment, the Unitigger module 104 computes a uniqueness statistic u based on the following equation:

$$u = (g*l - \log_c 2*(n-1)),$$

where g is the global fragment arrival rate, l is the length of the unitig beyond the average fragment length, and n is the number of fragments in the unitig. If u is greater than a genome-dependent threshold, then the Unitigger module 104 designates the unitig as a U-unitig. For the purposes of this invention, all unitigs that are not designated as U-unitigs are designated as R-unitigs.

The polishing step of the Unitigger module 104 identifies, marks, and may remove fragments and overlaps that interfere with the quality of the assembly. For example, chimeric fragments or fragments with fragment-ends that break potentially larger unitigs may be marked. In one embodiment, these fragments and their overlaps may also be removed.

For each U-unitig, the Unitigger module 104 determines how far its unitig-ends extend into repetitive regions of the genome. A repetitive region of the genome causes a branching in the graph at the ends of the U-unitigs. For each U-unitig, the Unitigger module 104 compares sequence information from its neighboring unitigs to determine the position in the U-unitig where the neighboring unitig sequences diverge, and designates this position as a branch point separating a unique region from a repetitive region. The Unitigger module 104 then performs a branch point selection graph reduction, removing any overlaps on the U-unitig that fall within a repetitive region. In one embodiment, when a U-unitig contains overlaps that extend past the branch point, any thinner overlaps that are entirely in the repetitive region of the U-unitig are removed.

Figure 2D:
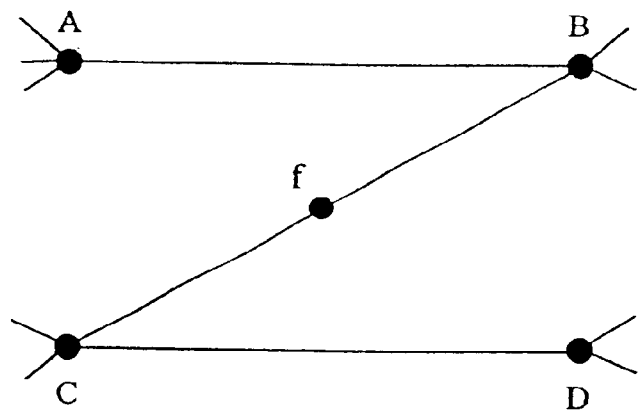
FIG. 2D provides a schematic representation of a chimeric fragment overlapping exactly two unitigs.

In one embodiment, the Unitigger module 104 identifies and may remove chimeric fragments. These are identified by searching the chunk graph for a characteristic pattern (refer to FIG. 2D): each end of the chimeric fragment (f) overlaps exactly one U-unitig (B and C), where each of these U-unitigs overlaps exactly one other U-unitig (A and D) on the same end that it overlaps the fragment f, and where U-unitigs A and D have no other overlaps on the ends that overlap U-unitigs B and C. In addition, $A \neq B$, $A \neq C$, $A \neq D$, $B \neq C$, $B \neq D$, and $C \neq D$.

Figure 2E:
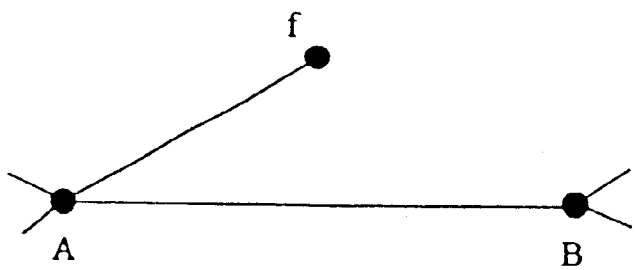
FIG. 2E provides a schematic representation of a fragment with a bad end sequence overlapping exactly one unitig.

In one embodiment, the Unitigger module 104 identifies and may remove fragments with bad end sequences. These are identified by searching the chunk graph for a characteristic pattern (refer to FIG. 2E): one end of the bad fragment (f) overlaps exactly one U-unitig (A) and the other end of fragment f has no overlaps. U-unitig A overlaps exactly one other U-unitig (B) on the same end that it overlaps fragment f, and U-unitig B has no other overlaps on the end that overlaps U-unitig A. In addition, $A \neq B$.

After the polishing step, the Unitigger module 104 merges any unitigs that can be joined in a unique manner by returning to the chunking step. The polishing and chunking steps may proceed iteratively until the number of changes falls below a predetermined threshold.

In one embodiment, the output of the Unitigger module 104 includes the set of unitigs, the information in each unitig including its consensus sequence, the position and orientation of all fragments belonging to it, and all remaining overlaps between unitigs. In a further embodiment, the unitig overlaps are classified by whether one or both of the unitigs connected by an overlap are wholly composed of globally contained fragments in the fragment overlap graph.

Scaffolder Module

Referring again to FIG. 1, the Scaffolder module 106 follows the Unitigger module 104. As shown in FIG. 1 the Scaffolder module 106 and the Repeat Resolution module 108 proceed iteratively, as will be discussed in detail below.

The Scaffolder module 106 takes as its input the set of unitigs and unitig overlaps produced by the Unitigger module 104 and mate pair data with putative statistics of the insert libraries from the shot-gun data set. The Scaffolder module 106 orders and orients the unitigs with respect to each other based on the mate pair information. If the two fragments of a mate pair belong to different unitigs, the Scaffolder module 106 infers a relative ordering, position, and orientation between those unitigs. The Scaffolder module 106 uses all of the pairwise inferences derived from the shot-gun data set's mate pair data to produce an overall ordering and orientation.

When there exists more than one mate pair between a pair of unitigs, multiple consistent mate pairs are bundled together into a weighted link (mate pair bundle) between the unitigs (an overlap that is consistent with the mate pairs will also be incorporated into the bundle). In order for mate pairs to be consistent they must imply the same orientation to the pair of unitigs. In addition a set of mate pairs (possibly including an overlap) is judged to be consistent if they agree on the distance between the unitigs—for instance by passing a chi squared test. Each mate pair or overlap provides an estimate of the distance between a pair of unitigs that can be viewed as a normally distributed stochastic measurement of the distance. These measurements are treated as independent random variables. A sample mean for the distance can be calculated as:

$$\text{distance\_mean} = \frac{\sum_i (mean_i / variance_i)}{\sum_i (1 / variance_i)}$$

where $mean_i$ is the mean of the estimated distance between unitigs implied by mate pair i or an overlap and variances is the variance of the estimated distance between unitigs implied by mate pair i or an overlap. A sample variance for the distance can be calculated as:

$$\text{distance\_variance} = \frac{1}{\sum_i (1 / variance_i)}$$

The candidate mate pair bundle is deemed to be consistent if the chi squared random variable X with n−1 degrees of freedom where n is the number of mate pairs in the bundle does not exceed a value that has a certain probability of occurring by random chance such as 1 in 1000:

$$X = \sum_{i=1}^{n} \frac{(mean_i - \text{distance\_mean})^2}{variance_i}$$

The mean and variance of a mate pair is based on the clone library from which the mate pair was selected. Clone library mean and variance estimates are part of the shot-gun data set inputs. By examining mate pairs where both fragments are contained in the same U-unitig the sample mean and variance for every clone library can be determined in the usual way (when a sufficient number of samples exist—otherwise the original estimates may be used) resulting in the $mean_i$ and $variance_1$ used in the equations above to estimate distances between unitigs. In one embodiment, mate pair bundle construction proceeds as follows: all mate pairs and overlaps between a pair of unitigs are determined; this set is partitioned into the four possible implied orientations of the unitigs; for each partition, the distance mean is determined and the chi squared test applied; if the chi squared test succeeds a mate pair bundle is constructed from the set with the calculated distance mean and variance; otherwise the chi squared test is computed for each set obtained by leaving one mate pair or overlap out of the set; if one or more succeed then, proceeding as before, a mate bundle using the lowest scoring set (smallest X) is constructed; otherwise a greedy, bottom-up clustering is performed using the chi square measure as a measure of distance/similarity between sets of mate pairs where a pair of sets is only clustered together if the resulting set passes the chi square test.

Because errors in mate pair data occur at a nonzero rate, and because repetitive regions can corrupt the scaffolding process, especially in the earlier stages, the Scaffolder module 106 first identifies pairwise orderings with the highest probability of being correct and unambiguous. In one embodiment, the Scaffolder module 106 first employs confirmed mate pairs whose fragments both belong to U-unitigs. A confirmed mate pair is one whose information is corroborated by at least one other mate pair. For example, if a first mate pair's fragments belong to unitigs X and Y, then the presence of a second mate pair whose fragments also belong to unitigs X and Y confirms the first mate pair;

the first mate pair in turn confirms the second mate pair. A mate pair can be confirmed directly or through a path of other corroborating mate pairs. In one embodiment, a mate pair is confirmed directly by being part of a mate pair bundle with at least two mate pairs in it.

The Scaffolder module 106 may represent the relationships between unitigs as a graph, with each vertex of the graph representing a unitig and each edge representing the set of consistent pairwise mate relationships that are confirmed between a pair of unitigs ("mate pair bundles"). The Scaffolder module 106 finds a consistent ordering of unitigs by performing a graph reduction, removing redundant and transitively inferable edges.

For the graph containing vertices that are U-unitigs, there should exist only one edge between any pair of vertices since U-unitigs should exist in only one orientation and distance from each other. If there exists more than one edge between a pair of U-unitigs, then the edge with the largest number of mate pairs is retained and the others are removed.

The graph is further reduced by removing transitively inferable edges in an analogous fashion to the reduction employed by the Unitigger module 104. There are two extensions to the transitive reduction. First, an edge can be removed by a path of any number of edges rather than only by a path of two edges, and the amount of discrepancy allowed between the distances of the edge and path edges is judged using a chi squared test rather than a small mismatch term. If removal of the edge would result in a statistically significant deviation from the expected length between unitigs, then the edge is not removed. Second, some branchings in the reduced graph can be removed by adding an edge that would then transitively reduce the edge causing the branching—this process is called smoothing.

Smoothing is necessary because, unlike in unitig reduction, where the edges are always overlaps (and hence there are no gaps between vertices joined by an edge), gaps do exist in the extended unitig graph between some unitigs, and the possibility exists that another unitig can fit into this gap. The smoothing is accomplished by examining each U-unitig end that has more than one mate pair bundle remaining after the redundant and transitive reductions and choosing the closest U-unitig based on the distance means for the mate pair bundles. The edge to the closest U-unitig ("nearest neighbor") is retained and the other edges are replaced by inferred edges from the nearest neighbor. If an inferred edge with high probability, using a chi squared test, implies that an overlap should exist but does not, then the smoothing fails for that end of the given U-unitig and the edges are changed back to the starting state. The smoothing is applied recursively because when the inferred edges are added they may cause branching at the nearest neighbor node. If the smoothing fails at any point in the recursion, the status of the edges is rolled back to the starting state.

After the graph has been reduced, the Scaffolder module 106 joins overlapping unitigs to form contigs. For the purposes of this invention, a "scaffold" refers to a set of unambiguously ordered contigs.

In one embodiment, the Scaffolder module 106 proceeds in several passes. For example, the first pass of the Scaffolder module 106 uses mate pair data generated from clone libraries of the shot-gun data set where the standard deviation of the clone lengths is on the order of or smaller than the smallest U-unitigs. The limit on the variance of the mate pair bundles used in the first phase reduces any chance of error in the transitive reduction and smoothing of the graph.

The second pass uses the scaffolds generated in the first pass as the vertices of the graph instead of the U-unitigs used in the first phase. Mate pairs from BAC fragments that have much higher variances are now combined with the already existing mate pairs as previously described to form mate pair bundles. Due to the larger variances, transitive reduction and smoothing are not performed. Instead, a greedy selection of the most reliable mate pair bundles (based on the number of mate pairs in the bundle) is used to construct much larger scaffolds by merging together the scaffolds generated in the first phase.

The Scaffolder module 106 also employs the derived clone library statistics to estimate the distance between contigs in the final ordering. The gap estimates are calculated by minimizing the squared difference between the predicted clone lengths and the mean clone length normalized by the clone variance for all clones spanning a gap. Standard linear algebra routines are used to minimize:

$$Error = \sum_i \frac{(clone\_mean_i - predicted\_clone\_length_i)^2}{clone\_variance_i}$$

where $clone\_mean_i$ is the mean for the clone library that mate pair i is selected from, $clone\_variance_i$ is the variance for the clone library from which mate pair i is selected. The $predicted\_clone\_length_i$ is the length that the clone for mate pair i would be if the gaps that the clone spans are represented as variables to be solved for:

$$predicted\_clone\_length_i = base\_pair\_constant$$

$$predicted\_clone\_length_i = base\_pair\_constant + \sum_j gap_j$$

where $base\_pair\_constant$ is the amount of base pairs in the contigs that mate pair i spans and $gap_j$ is a variable representing the length of one of the gaps that is spanned by mate pair i.

In one embodiment, the output of the Scaffolder module 106 includes an unambiguously ordered set of contigs. In a further embodiment, the output of the Scaffolder module 106 includes estimates of the distances between the ordered contigs.

Repeat Resolution Module

Referring still to FIG. 1, the Repeat Resolution module 108 follows the Scaffolder module 106. As shown in FIG. 1 the Scaffolder module 106 and the Repeat Resolution module 108 proceed iteratively.

For the purposes of this invention, the term "R-unitig" is used to refer to those unitigs that the Unitigger module 104 is not able to characterize as a unique U-unitig. The Repeat Resolution module 108 determines the positions of the R-unitigs relative to the scaffolds produced by the Scaffolder module 106. In one embodiment, the Repeat Resolution module 108 fills gaps within and between the scaffolds, resulting in a full assembly of sequence data that covers the entire genome.

The Repeat Resolution module 108 employs overlap and mate pair data to determine the position of an R-unitig. It is expected that mate pair data is typically more reliable than overlap data in this context. The position of an R-unitig could be within a single scaffold, or between two or more distinct scaffolds. Experimental data suggests that most unitigs, as assembled, will contain fragments from only a single region of the genome. Thus, initial tests on a unitig can regard it as an atomic element. When there is sufficient evidence that a unitig is not from a single region of the genome, the Repeat Resolution module 108 will attempt to break it apart.

Figure 3:
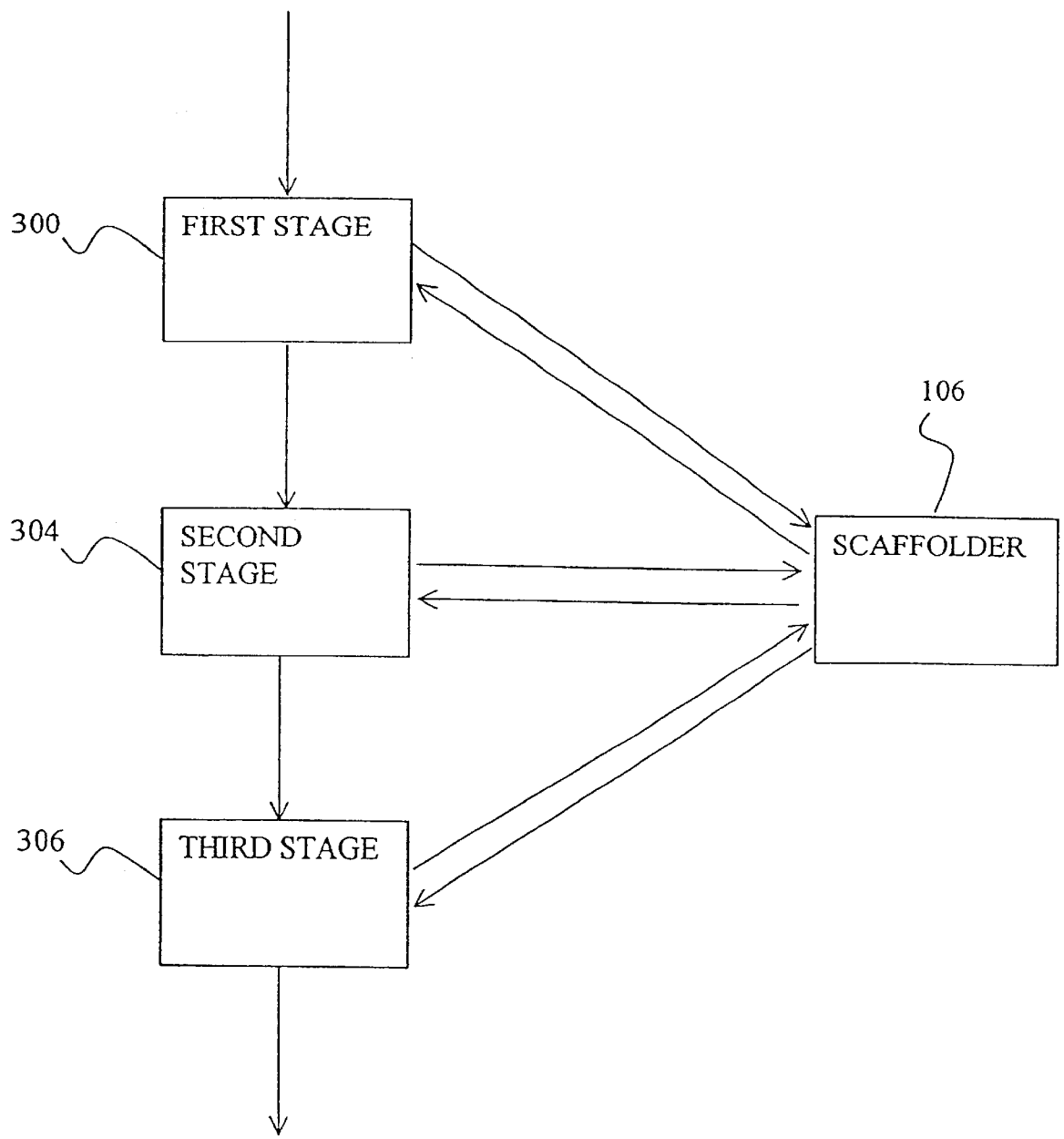
FIG. 3 provides a flow diagram of one embodiment of a Repeat Resolution module.

The Repeat Resolution module 108 applies a series of decreasingly rigorous tests in an attempt to assign a position to each R-unitig or various subsets of its fragments. In a further embodiment, as illustrated in FIG. 3, the Repeat Resolution module 108 employs three consecutive stages 300, 304, and 306, each of which is less conservative than the former.

Experimental data suggest that repetitive sequences have a certain amount of micro-heterogeneity. Multi-alignment mismatches that have a high quality value are likely due to micro-heterogeneity between different instances of a repeat rather than a result of sequencing errors. This evidence is even stronger when differences occur at corresponding positions in the multi-alignment of fragments in an R-unitig. An R-unitig multi-alignment is termed "repetitive" if it contains fragments from multiple locations in the genome. The multi-alignment is termed "normal" if all fragments belong in only one location. Since repetitive sequences in different locations in the genome tend to be mutated, all fragments in a group (i.e., those coming from the same location) should have the same mutated character(s) with the exception of those due to sequencing errors. This feature distinguishes the different multi-alignment types from each other. An example of a repetitive alignment is depicted in FIG. 4A. In the displayed alignment, dots represent the underlying character displayed in the first row and each pair of consecutive rows belongs to a different group.

To distinguish a repetitive alignment from a normal alignment there must be at least two groups that contain more than one fragment. Therefore the lower bound on the number of fragments that must be in a repetitive multiple alignment is four. In one embodiment, a one-sided statistical test is computed to determine if the observed alignment is normal. Each column in the alignment is assigned a predicate $P_{ij}$ that depends on rows i and j. This predicate is defined in such a way that it occurs with probability p(s) in a normal alignment where p(s) depends on the average sequencing error rate. Hence the number of columns that have this predicate is a random variable Q that is binomially distributed with a mean of $1*p(s)$. The predicate $P_{ij}$ of a column in a repetitive alignment ought to have a much higher probability of occurring for at least one pair of rows. If the observed alignment contains x columns with the predicate P, the hypothesis $H0:x \leq 1*p(s)$ can be tested for a given level of significance, $\alpha$. A column has the predicate $P_{ij}$ if it contains the same character c in rows i and j different from the majority character of the column. Given the sequencing error rate, s, which can be estimated from the given alignment, the probability of a column having this predicate can be computed as follows:

In rows other than i and j, any characters may be present as long as the character c occurring in rows i and j does not become the majority character. This allows computation of the probability of all possible events in the remaining rows by summing up the probabilities of a four-nomial distribution yielding a probability P(c).

For the two rows (i and j) there are two possibilities. First, the character c in the two fixed rows has changed from the underlying sequence. This event happens with probability $(s/4)^2$ for each of the four characters into which the underlying character can change. Second, the character c in the two fixed rows has not changed from the underlying sequence. This event happens with probability $(1-s)^2$.

Hence, assuming that c1,c2,c3,c4 are the characters that differ from the underlying character u, the overall probability of the predicate $P_{ij}$ is $$(1-s)^2 * P(u) + \sum_{i=1}^{4} P(c_i) * (s/4)^2$$

Not all repetitive multi-alignments have more columns with predicate $P_{ij}$ than a normal alignment for a particular pair i, j. The key observation is that a repetitive alignment is very likely to have some pair of rows, say i' and j' that have the predicate $P_{i'j'}$. Therefore the test is conducted for each pair i,j of rows (t=(l choose 2) tests). If the null hypothesis is rejected for one pair, then the alignment is assumed to be repetitive. Conducting this greater number of tests increases the chance of incorrectly rejecting the null hypothesis from $\alpha$ to $1-(1-\alpha)^t$. To maintain a confidence level of $\alpha$, each test must be conducted with a level of significance of $1-(1-\alpha)^{1/t}$.

In one embodiment, the described test can be used to break apart repetitive R-unitigs. Two rows i and j with the predicate $P_{ij}$ are located and used as a seed to find fragments that belong to the same repeat instance. These fragments can then be removed from the alignment and the test can be repeated until the remaining alignment is normal.

Referring again to FIG. 3, the first stage 300 of the Repeat Resolution module 108 identifies R-unitigs with non-conflicting, sufficiently strong, and corroborated evidence indicating their position within a scaffold gap. The regions before the first unitig in a scaffold and after the last unitig in a scaffold are also regarded as gaps.

These R-unitigs are identified by the presence of two or more mate-pair links to previously scaffolded unitigs that all indicate the same position within a scaffold. If there are exactly two mate-pair links, no mate-pair links indicating a contradictory scaffold position are allowed. If three or more mate-pair links indicate a consistent position, then a single contradictory link is allowed. R-unitigs with at least two mate-pair links to each of two scaffolds, indicating a position off the end of each of those scaffolds, are also allowed if there is a scaffold link that is consistent with the distance and orientation of those two scaffolds implied by the position of the R-unitig. In one embodiment, links to as-yet-unscaffolded unitigs are ignored. In another embodiment such links are regarded as contradictory.

The Repeat Resolution module 108 then checks for consistency of all such R-unitigs assigned to the same scaffold gap. Based on positions of the unitigs determined from the mate-link information, all implied overlaps between two R-unitigs, and between an R-unitig and a scaffold unitig, are checked. If a single R-unitig causes all overlap failures, it is eliminated from further consideration in this phase. If several R-unitigs do not have their indicated overlaps, all the R-unitigs assigned to that scaffold gap are eliminated from further processing in this phase. Mate-pair links between R-unitigs in the same gap are also checked for consistency.

In one embodiment, an additional check is made that there exists a path of overlapping unitigs that connects the scaffold unitigs that bound the gap being processed and that includes as many R-unitigs in that gap, at their indicated position and orientation, as possible. R-unitigs not contained in this path are eliminated from further consideration in this phase. For gaps at scaffold ends, the overlap path merely extends from the end unitig of the scaffold, with no fixed destination.

The Repeat Resolution module 108 then inserts the R-unitigs that pass the above consistency checks into the scaffolds, and invokes the Scaffolder module 106 with the newly modified scaffolds as input. This first stage of the Repeat Resolution module 108 is then repeated using the output of the Scaffolder module 106. This process is iterated until the number of R-unitigs inserted in an iteration falls below a predetermined threshold.

The Repeat Resolution module 108 may employ an additional stage between the first stage and the second stage. In this additional stage, the Repeat Resolution module 108 performs scaffold merging. In this embodiment, distinct scaffolds are merged using mate pair data derived from BAC fragments.

In the second stage 304, the Repeat Resolution module 108 identifies R-unitigs and places them into scaffolds in a manner similar to the first stage 300. However, in this stage, the Repeat Resolution module 108 uses inferred information in contrast to the confirmed information used in the first stage. In this stage, the information is inferred through a process called "stone throwing." In this process, the module 304 provisionally places in a scaffold gap a set of R-unitigs, called "stones," that have at least one mate-link to a unitig in that scaffold indicating the tentative position. A stone may be placed in more than one position if it has multiple links indicating such positions.

The module 304 then attempts to confirm the placement of each stone by finding a path of overlapping unitigs connecting the scaffold unitigs bounding the gap and passing through the stone in its tentative position and orientation. For gaps at scaffold ends, the overlap path merely extends from the end unitig of the scaffold, with no fixed destination.

If a path is found that confirms the position and orientation of the stone, a copy of that stone's R-unitig is placed in the scaffold. More than one copy of the same R-unitig may be placed in this manner, indicating the unitig contains fragments from more than one copy of a repeat sequence in the genome. In this case, the fragments comprising the R-unitig can be assigned to the separate copies in a later stage of the assembly.

In a manner similar to the first stage, the Scaffolder module 106 is invoked, the second stage is then repeated using the output of the Scaffolder module 106, and this process is iterated until the number of insertions made in an iteration falls below a predetermined threshold. In an alternate embodiment, exactly one iteration of this second stage is employed.

In the third stage 306, the Repeat Resolution module 108 attempts to fill the remaining scaffold gaps by calculating overlap quality values for overlaps between unitigs and employing these overlap quality values to guide traversals of overlap graphs covering scaffold gaps. In one embodiment, the calculated overlap quality value reflects whether the two unitigs stem from the same or different genomic regions; a high overlap quality value indicates a "normal" overlap from the same genomic region and a low overlap quality value indicates a "repetitive" overlap, presumably from different genomic regions. In this embodiment, the overlap quality value is calculated based on a statistical model that compares the likelihood of the overlap occurring under the two assumptions that the overlap is normal or repetitive. The Repeat Resolution module 108 attempts to traverse the overlap graph using a depth-first search choosing the edge with the highest overlap quality value. A traversal is deemed successful if the other end of the gap is reached within length constraints imposed by the gap. In another embodiment this walk also makes use of mate links to confirm its decisions.

In one embodiment, a statistical model is employed for deriving the overlap quality values that guide the walk as follows. Given two overlapping sequences and their sequencing quality values, an alignment of the two strings is computed. This yields two aligned, gapped strings with assigned sequencing quality values as shown FIG. 4B. The quality value of an unaligned residue is either set to the average quality of the whole sequence or derived from neighboring quality values. This embodiment employs a Bayesian approach similar to that outlined in Marth et al. Nat Genet 1999 Dec. 23(4):452–6 to compute the probability that the observed data fits one of two following models:

MN=the alignment is normal and therefore the mutations are due to sequencing errors.

MR=the alignment is repetitive and therefore the mutations are due to sequencing errors and mutations.

For a repetitive alignment we expect 1) a higher overall error rate in the alignment than one would expect given the quality values; and 2) more high quality mismatches—mismatches where both positions have a high sequencing quality value. This results in a low probability P(MN|D), whereas we expect a higher P(MN|D) for normal alignments. These probabilities are used to assign a higher overlap quality value in the case of a normal alignment and a lower overlap quality value in the case of a repetitive alignment.

The approach is based on the number D(qt) of mismatches in the alignment (indels and substitutions) in which both positions have a quality value of at least qt. In one embodiment, the average probability that a function has a qt-mismatch is inferred by using the quality values of the matching region where the quality of a dash is arbitrarily set to the quality of a neighboring character or to the average quality of the sequence. From this, an average sequencing error rate, s, may be determined. Next, a value x is selected to be the minimum percent difference between paralogous sequences, omitting SNPs.

For normal alignments, P(MN|D) should be higher than P(MR|D), and this probability is used as a quality measure. If model MN is true, DN=s*l mismatches should occur on average. If model MR is true, DR=(s+x)*l mismatches should occur on average, where l is the length of the alignment.

Bayes' formula yields:

$$P(MN \mid D) = \frac{P(D \mid MN) * P(MN)}{P(D \mid MN) * P(MN) + P(D \mid MR) * P(MR)}$$

Since the prior probabilities of the two models are not known, they are assumed to be equally weighted. In this case the formula simplifies to:

$$P(MN \mid D) = \frac{P(D \mid MN)}{P(D \mid MN) + P(D \mid MR)}$$

where the probabilities P(D|MN) and P(D|MR) must be approximated. In one embodiment, this is accomplished by assuming for MN a Poisson distribution with parameter λ=DN and for MR a Poisson distribution with parameter λ=DR. This yields:

$$P(MN|D)=1/(1+((s+x)/s)^D e^{-lx})$$

This probability becomes increasingly discriminating with longer alignments. Since the above probability is dependent on the length of the alignment it is not clear at what value the threshold should be set for a given length such that a given success rate would be expected. In one embodiment, a series of simulation experiments are performed to set thresholds for different alignment lengths to achieve a pre-selected average rate of success. The thresholds are then used to devise a quality score that is independent of the length of a given alignment.

In one embodiment, the final output of the Repeat Resolution module 108 includes a scaffold having the relative ordering, position, and orientation of substantially all fragment data in the shot-gun data set.

In another embodiment, for R-unitigs that are placed by stage 304 or stage 306, the fragments are divided among the placed copies of the R-unitigs according to quality values and mate information. Then in a final step a new consensus sequence is computed which reflects the separation of the fragments.

Consensus Module

Referring again to FIG. 1, the Consensus module 100 follows the Repeat Resolution module 108, and is the final step of the assembler. In one embodiment, the Consensus module 110 may also be invoked by earlier modules, such as the Unitigger module 104. In the final stage, the Consensus module 110 generates a consensus sequence for each contig produced by the Scaffolder module 106.

The Consensus module 110 processes input on a contig-by-contig basis. For each contig, the Consensus module 110 first generates and refines a multi-alignment, then assigns a base to each position in the contig based on a scoring of the appropriate column in the multi-alignment.

In one embodiment, the input to the Consensus module 110 includes a contig having a list of fragments, their layout positions, and a pointer to a valid data store for retrieving sequence information. In a further embodiment, the output of the Consensus module 110 includes a multi-alignment of the fragment data, a consensus sequence for the calculated multi-alignment, and quality values for each position in the consensus sequence.

As used herein, the term "surrogate" refers to an unresolved sub-assembly within a contig, also known as an overcompressed repetitive unitig. A unitig may contain fragments from different parts of the genome, yet the fragment sequence agrees sufficiently to form a consistent multi-alignment and derive a consensus sequence for the repetitive region. As the Scaffolder module 106 builds contigs from unitigs, it may tentatively place a repetitive unitig in a contig with only its consensus sequence, as determined by a previous invocation of the Consensus module 110, and leave resolution or placement of individual component fragments to a later stage.

In one embodiment, the Consensus module 110 generates a contig's consensus sequence in three stages. In the first stage, the Consensus module 110 generates the initial multi-alignment. In the second stage, the Consensus module 110 refines the multi-alignment. In the final stage, the Consensus module 110 makes base calls at each position in the consensus sequence and associates a quality value with each call.

The first stage of the Consensus module 110 begins by ordering the contig's fragments by starting position within the contig. The Consensus module 110 then assembles the fragments into a multi-alignment in a pairwise fashion, using a dynamic-programming algorithm to calculate the pairwise alignments. Each fragment is aligned to the previously-aligned fragment with maximum overlap based on the initial position information. Once the multi-alignment has been constructed, the Consensus module 110 generates a consensus sequence by calling bases in each column of the multi-alignment with a simple consensus model. In one embodiment, the Consensus module 110 breaks ties using the sum of quality values. In an alternative embodiment, the Consensus module 110 breaks ties at random.

In the second stage, the Consensus module 110 employs a window-based refinement process to sweep across the multi-alignment produced by the first stage. This process looks for gappy regions and locally corrects the alignment within a window containing such a region. For the purposes of this invention, the term "gappy" is used to refer to a region of high edit score on a multi-alignment.

Experimental data supports the use of an "abacus" algorithm to correct the alignment within a window. In one embodiment, the second stage of the Consensus module 110 performs the following abacus algorithm: (1) select a window around the gappy region using anchored regions of strong alignment as the window's borders, and insert a gap column on the left of the window; (2) seed the first position in the new gap column with the first base in the first non-gap column of the sequences in the window; (3) sweep through the columns from left to right, and for each column, shift each base to the left as far as possible across at least one gap position to align with a previous matching column, if such a move would reduce the cumulative edit score within the previously swept columns in the window; (4) repeat steps (1)–(3), moving across the window from right to left; and (5) compare the left-to-right alignment with the right-to-left alignment, and keep the alignment with the lower edit score.

In the final stage, the Consensus module 110 generates a base call for each column and associates quality values with each call. In one embodiment, the Consensus module 110 employs a statistical model to distinguish between single nucleotide polymorphisms ("SNPs") and sequencing errors to make a base call. In this embodiment, the quantity $q_i$ represents the quality value of fragment data at position i and $q_i$ is interpreted according to the following equation:

$$q_i = -10\log_{10}(p_i),$$

where $p_i$ is the probability of an error in the base call at position i.

By way of example, consider a multi-alignment including sequence data from two sequenced haplotypes. For each column of the multi-alignment, the potential underlying events E can be partitioned into $E_a$ and $E_p$, representing the absence or presence of a single nucleotide polymorphism ("SNP") event, respectively. This partitioning can be expressed by the following equation:

$$E = E_a \cup E_p = \{a : a \in A\} \cup \{\rho = ab : a, b \mathring{A} A, a \neq b\}$$

For each potential underlying event e in E, the conditional probability of observing the observed column data given the underlying event, $\tau_e$, can be calculated by the following equation:

$$\tau_e = \begin{cases} \prod_{i=1}^{n} \left( (b_i == e) ? (1 - p_i(b_i)) : \frac{1}{(|E_a| - 1)} p_i(b_i) \right) & \text{for } e \in E_a \\ \tau_a + \tau_b & \text{for } e \in E_p \end{cases}$$

In this equation, n is the number of bases in the column, and $p_i(b_i)$ is the probability of error in the base call for base $b_i$.

The probability of the underlying event, π(e), can be then be calculated according to the Bayesian formula:

$$\pi(e) = \frac{P(e)\tau_e}{\sum_{x \in E} P(x)\tau_x}$$

In this equation, P(e) represents the a priori probability of an event e. The Consensus module 110 then chooses the underlying event with the highest probability as the consensus base call for that column. The associated quality value is calculated from the probability of error, 1−π(e).

In one embodiment, the a priori probabilities associated with each event are tunable parameters to the Consensus module 110. Considerations in determining these parameters can include the column neighborhood, the global abundance of each base, the number of haplotypes to allow in the output data, the estimated SNP frequency, and the estimated sequencing error. In this embodiment, if the number of haplotypes allowed in the output data is set to 1, SNP calls may be eliminated.

Assembler Core

Figure 5:
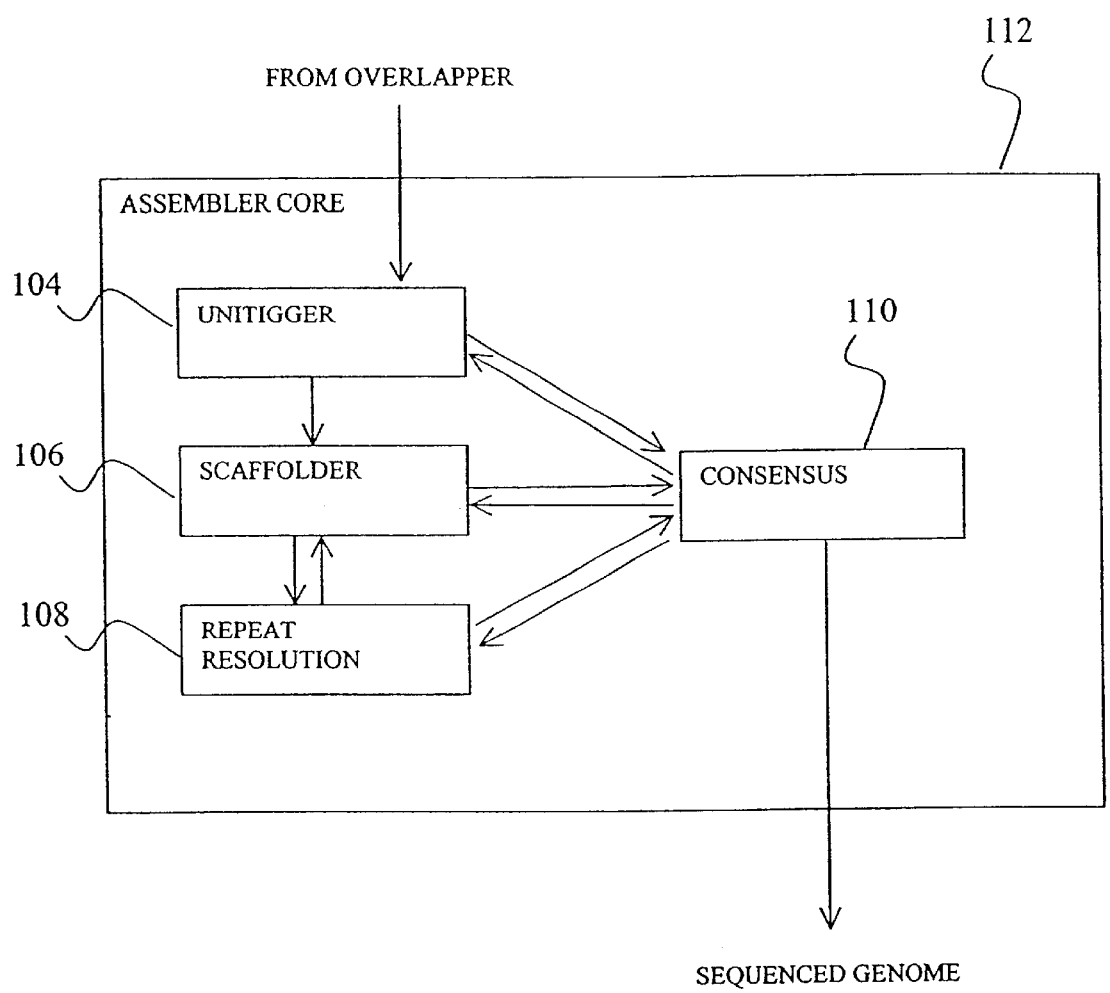
FIG. 5 provides a flow diagram of one embodiment of an assembler core.

In one embodiment, as illustrated in FIG. 5, the assembler of this invention includes an assembler core 112 having a Unitigger module 104, a Scaffolder module 106, a Repeat Resolution module 108, and a Consensus module 110. The Unitigger module 104 receives input from the Overlapper module 102, identifies unitigs, and invokes the Consensus module 110 for each unitig. The Scaffolder module 106 positions unitigs with respect to each other, and invokes the Consensus module 110 on the sequence information associated with the unitigs. The Repeat Resolution module 108 attempts to place repetitive sequences into scaffolds and invokes the Scaffolder module 106 to build revised scaffolds, based on the placement of the repetitive sequences. Finally, the Consensus module 110 is run one last time to produce the sequenced genome.

Other methods of interaction between the modules are contemplated. Furthermore, varying the order of invocation of the modules is also contemplated.

Simulator

Another aspect of the present invention is to provide a method of generating a simulated shot-gun data set. Such a simulated data-set can be used in designing, implementing, testing, and tuning an assembler, such as the assembler of the present invention. Parameters for each of the above modules may be determined and refined through the use of a simulator.

In one embodiment, the simulator produces a synthetic genome and generates a synthetic shot-gun data set from it. Synthetic genomes are described in terms of their repeat structure expressed as a stochastic grammar. Examples of parameters include the number of copies of a given repeat, mutation errors to be inserted, and the frequency that the repeat element is fractured, so that only a partial element is inserted. Repeat elements can be constructed hierarchically from other repeat elements, or can be defined by a constant sequence input from a file.

The synthetic genome is "shot-gunned" into a collection of synthetic inserts, which are then used to generate synthetic fragment libraries, each library representing reads from the end of synthetic inserts of a particular statistical nature. The resulting synthetic shot-gun data set includes sequence information for each fragment, as well as mate pair relationships between the fragments. Parameters of the shot-gunning include probability distributions for insert length, read lengths, clear ranges, and sequence error rate. When a synthetic genome is shot-gunned, the simulator maintains for each generated fragment the location within the synthetic genome from which the fragment was "cut," as well as the repeat elements that contribute sequence to the fragment.

Certain novel aspects of the simulator include its ability to represent fractured repeat elements and the maintenance of repeat annotation on the fragments that are output.

Equivalents

The invention may be embodied in other specific forms without departing from the spirit or essential characteristics thereof. The foregoing embodiments are therefore to be considered in all respects illustrative, rather than limiting, of the invention described herein. Scope of the invention is thus indicated by the appended claims, rather than by the foregoing description, and all variants which fall within the meaning and range of equivalency of the claims are therefore intended to be embraced therein.

What is claimed is:

1. A method for generating a consensus nucleotide sequence corresponding to a nucleotide sequence in a genome from a shot-gun data set comprising a plurality of fragments comprising nucleotide sequence data selected at random from a genome that corresponds to nucleotide sequences of the genome, said shot-gun data set further comprising mate pair data, wherein a mate pair comprises a pair of end reads collected from both ends of an insert and a distance measure indicating the distance between said pair of end reads, such that said consensus nucleotide sequence comprises a nucleotide sequence of said genome in machine-readable form, said method comprising the steps of:

(a) identifying a first set of fragments from said shot-gun data set, wherein each fragment in said first set contains a screen item;
   (b) generating a second set of fragments by excluding said first set from said shot-gun data set;
   (c) generating an overlap data set by performing a plurality of pair-wise comparisons between said fragments of said second set to determine the presence of similar nucleotide sequences in each pair, wherein said second set does not contain said screen items;
   (d) performing a graph reduction on said overlap data set, thereby producing a minimal subgraph;
   (e) designating a plurality of non-branching portions of said minimal subgraph as a plurality of unitigs;
   (f) generating a scaffold, wherein said scaffold comprises the relative order of said plurality of unitigs with respect to one another calculated from said mate pair data;
   (g) generating at least one multi-alignment calculated from said scaffold; and
   (h) generating a consensus sequence calculated from said multi-alignment.

2. The method of claim 1 wherein said identifying step (a) comprises the substeps of:

(i) generating a look-up table comprising the sequence information of said set of fragments;
   (ii) populating a hit accumulator with hit data, said hit data representing matches between said screen item and said set of fragments;
   (iii) transferring said hit data from said hit accumulator to a hit analyzer; and (iv) employing said hit analyzer to determine the presence of said screen item in said subset.

3. The method of claim 2 wherein said hit accumulator comprises a data structure stored on a computer-readable medium and represents an accumulation of matches between a screen item and a plurality of fragments, the data structure comprising an array of stacks, said array indexed by diagonal, said stacks comprising first-in-first-out ("FIFO") queues for hit data.

4. The method of claim 2 wherein said hit analyzer comprises a data structure stored on a computer-readable medium and represents a plurality of matches between a screen item and a plurality of fragments, said fragments being subdivided by block, said data structure comprising a ring of sparse arrays, said sparse arrays being indexed by fragment and subindexed by block.

5. The method of claim 1 wherein said overlap data generating step (c) comprises the substeps of:

(i) providing a set of fragment overlap data; and (ii) generating an all-against-all fragment overlap graph from said fragment overlap data;

and wherein said unitig designating step (e) comprises the substeps of:

(i) performing a graph reduction on said all-against-all overlap graph generated in step (c), producing a minimal subgraph; and (ii) designating non-branching portions of said minimal sub-graph as a unique sub-assembly.

6. The method of claim 5 wherein said unitig designating step (e) further comprises the step of determining whether said unique sub-assembly comprises nucleotide sequence information corresponding to a unique region of a genome.

7. The method of claim 6 wherein said determination is performed using arrival rate statistics.

8. The method of claim 1 wherein the calculation of said relative order of said plurality of unitigs in said scaffold generating step (f) comprises the step of determining the relative order of a pair of unitigs which comprises:

(i) identifying a mate pair wherein a first end read of said mate pair belongs to a first unitig and a second end read of said mate pair belongs to a second unitig; and (ii) determining a position and orientation of said first and second unitigs relative to each other based on said mate pair.

9. The method of claim 8 wherein said scaffold generating step (f) further comprises the step of confirming said relative position and orientation of said unitigs by identifying a second mate pair having information consistent with the mate pair identified in said identifying step (i).

10. The method of claim 1 wherein said scaffold generating step (f) further comprises the step of filling a gap in the scaffold with a unitig, which comprises:

(i) identifying a mate pair comprising a fragment belonging to a U-unitig bordering a scaffold gap;

(ii) providing an all-against-all overlap graph;

(iii) traversing said overlap graph from said U-unitig to said unitig, said traversal being consistent with length and quality parameters; and (iv) adding said unitig to said scaffold.

11. The method of claim 1 wherein said consensus sequence generating step (h) comprises the steps of:

(i) refining said multi-alignment; and (ii) determining a base call for each position in said multi-alignment.

12. The method of claim 11, wherein said multi-alignment refining step (i) comprises the steps of:

(A) identifying a region having a high edit score;

(B) identifying left and right borders of said region;

(C) inserting a column at said left border;

(D) sweeping from left to right, moving bases leftward if such a move would decrease the edit score;

(E) repeating step (D) from right to left;

(F) comparing alignment produced by step (D) to that produced by step (E); and (G) keeping the alignment with lowest edit score.

13. The method of claim 11, wherein said base calling step (ii) comprises the steps of:

(A) for each potential underlying event, generating a conditional probability of said event given observed data;

(B) based on said conditional probabilities, calculating an overall probability of said event; and (C) base calling a base corresponding to highest overall probability.

14. The method of claim 13 further comprising the step of calculating an associated quality value based on said overall probability.

15. The method of claim 13 wherein said calculating step (B) is performed according to a Bayesian equation.

16. The method of claim 15 wherein a priori probabilities of said meter selected from the group consisting of:

column neighborhood, global abundance of each base, number of haplotypes allowed in sequencing error.

* * * * *

UNITED STATES PATENT AND TRADEMARK OFFICE
CERTIFICATE OF CORRECTION

PATENT NO. : 6,714,874 B1
DATED : March 30, 2004
INVENTOR(S) : Myers et al.

It is certified that error appears in the above-identified patent and that said Letters Patent is hereby corrected as shown below:

<u>Column 28,</u>
Line 45, "The method of claim 15 wherein a priori probabilities of said meter selected from the group consisting of:" should read -- The method of claim 15 wherein prior probabilities of said Bayesian equation are calculated according to a parameter selected from the group consisting of: --.

Signed and Sealed this

Fourth Day of April, 2006

JON W. DUDAS
*Director of the United States Patent and Trademark Office*